(12) United States Patent
Jang et al.

(10) Patent No.: US 8,323,933 B2
(45) Date of Patent: Dec. 4, 2012

(54) VECTOR FOR TRANSFORMATION USING TRANSPOSONS, MICROORGANISMS TRANSFORMED BY THE VECTOR, AND METHOD FOR PRODUCING L-LYSINE USING THE SAME

(75) Inventors: Jae-Woo Jang, Gyeonggi-do (KR); Sang-Jo Lim, Incheon (KR); Jong-Soo Choi, Seoul (KR); Chul-Ha Kim, Seoul (KR)

(73) Assignee: CJ Cheiljedang Corporation (KR)

( * ) Notice: Subject to any disclaimer, the term of this patent is extended or adjusted under 35 U.S.C. 154(b) by 0 days.

(21) Appl. No.: 12/867,649

(22) PCT Filed: Apr. 10, 2009

(86) PCT No.: PCT/KR2009/001845
§ 371 (c)(1),
(2), (4) Date: Aug. 13, 2010

(87) PCT Pub. No.: WO2009/125992
PCT Pub. Date: Oct. 15, 2009

(65) Prior Publication Data
US 2010/0330624 A1  Dec. 30, 2010

(30) Foreign Application Priority Data
Apr. 10, 2008 (KR) ........................ 10-2008-0033054

(51) Int. Cl.
*C12P 13/08* (2006.01)
*C12N 9/00* (2006.01)
*C12N 1/20* (2006.01)
*C12N 15/00* (2006.01)
*C07H 21/04* (2006.01)

(52) U.S. Cl. ..................... 435/115; 435/183; 435/252.3; 435/320.1; 536/23.2

(58) Field of Classification Search .................. None
See application file for complete search history.

(56) References Cited

U.S. PATENT DOCUMENTS

| | | | |
|---|---|---|---|
| 5,457,040 A | 10/1995 | Jarry et al. | |
| 5,633,154 A | 5/1997 | Schaefer et al. | |
| 5,804,414 A | 9/1998 | Moriya | |
| 6,200,785 B1 | 3/2001 | Kreutzer et al. | |
| 6,221,636 B1 | 4/2001 | Hayakawa et al. | |
| 6,740,742 B2 | 5/2004 | Mackel et al. | |
| 6,746,855 B2 | 6/2004 | Kreutzer et al. | |
| 6,861,246 B2 | 3/2005 | Kreutzer et al. | |
| 6,872,553 B2 | 3/2005 | Eikmanns et al. | |
| 6,913,909 B2 | 7/2005 | Ziegler et al. | |
| 6,962,989 B1 | 11/2005 | Pompejus et al. | |
| 7,160,711 B2 | 1/2007 | Bathe et al. | |
| 8,048,650 B2 | 11/2011 | Koo et al. | |
| 8,058,036 B2 | 11/2011 | Koo et al. | |
| 2002/0055153 A1 | 5/2002 | Kreutzer et al. | |
| 2002/0192674 A1 | 12/2002 | Hermann et al. | |
| 2002/0197605 A1 | 12/2002 | Nakagawa | |
| 2003/0055232 A1 | 3/2003 | Li et al. | |
| 2005/0153402 A1 | 7/2005 | Pompejus et al. | |
| 2005/0255568 A1 | 11/2005 | Bailey et al. | |
| 2006/0084152 A1 | 4/2006 | Pompejus et al. | |
| 2008/0293100 A1 | 11/2008 | Wendisch et al. | |
| 2010/0015673 A1 | 1/2010 | Koo et al. | |
| 2010/0028957 A1 | 2/2010 | Koo et al. | |
| 2010/0129884 A1 | 5/2010 | Cho et al. | |

FOREIGN PATENT DOCUMENTS

| | | |
|---|---|---|
| CN | 1187540 A | 7/1998 |
| DE | 101 10 760 A1 | 8/2001 |
| EP | 0733710 A1 | 9/1996 |
| EP | 0854189 A2 | 7/1998 |
| EP | 1715055 | 10/2006 |
| JP | 62-079788 A | 4/1987 |
| JP | Hei 7-121228 | 12/1995 |
| JP | 09-070291 | 3/1997 |
| JP | 10-215883 A | 8/1998 |
| JP | 2001-037495 A | 2/2001 |
| JP | 2002-508921 A | 3/2002 |
| JP | 2003-503006 A | 1/2003 |
| JP | 2006-512922 | 4/2006 |
| KR | 10-0313134 | 10/2001 |
| KR | 1020050065712 | 6/2005 |
| KR | 1020050065712 A | 6/2005 |
| KR | 1020060068505 A | 6/2006 |
| KR | 10-2008-025355 A | 3/2008 |
| WO | WO 92/02627 | 2/1992 |
| WO | WO 02/053707 | 7/2002 |
| WO | 2005/121349 A2 | 12/2005 |
| WO | WO 2005/121349 | 12/2005 |
| WO | 2006/065095 A1 | 6/2006 |
| WO | 2006/071099 A1 | 7/2006 |
| WO | WO 2007/039532 | 4/2007 |
| WO | WO 2008/033001 * | 3/2008 |

OTHER PUBLICATIONS

Hayashi et al. Applied Microbiology and Biotechnology (2006), 72(4), 783-789.*
Accession AX121271. May 11, 2001.*
Tangney et al. Journal of Molecular Microbiology and Biotechnology (2000), 2(1), 71-80 (Abstract).*
Office Action issued Jan. 12, 2011 in U.S. Appl. No. 12/518,578.
Office Action issued Jan. 7, 2011 in U.S. Appl. No. 12/518,572.
Office Action issued Jul. 6, 2011 in U.S. Appl. No. 12/518,572.
Office action issued Jul. 11, 2011 in U.S. Appl. No. 12/518,578.
International Search Report issued in PCT/KR2009/001845 mailed Nov. 27, 2009.
Mormann (Aug. 10, 2006) BMC Genomics, 7:205, doi:10.1186/1471-2164-205, "Random mutagenesis in *Corynebacterium glutamicum* ATCC 13032 using an IS6100-based transposon vector identified the last unknown gene in the histidine biosynthesis pathway".
Peters-Wendisch et al. (Nov. 2005) Applied and Environmental Microbiology, 71(11):7139-7144, "Metabolic Engineering of *Corynebacterium glutamicum* for L-Serine Production".

(Continued)

*Primary Examiner* — Christian Fronda
(74) *Attorney, Agent, or Firm* — Swanson & Bratschun, L.L.C.

(57) ABSTRACT

The present invention relates to a vector for transformation using transposon genes, microorganisms transformed by the vector, and a method for producing L-lysine using the microorganisms.

14 Claims, 4 Drawing Sheets

OTHER PUBLICATIONS

Tsuge et al. (2005) Microbiology 151:501-508, "A New Insertion Sequence, ISI4999, from *Corynebacterium glutamicum*".

PCT International Preliminary Report on Patentability issued Oct. 12, 2010 and Written Opinion for PCT/KR2009/001845.

Hayes, Finbarr (2003) Annu. Rev. Genet. 37:3-29, "Transposon-Based Strategies for Microbial Functional Genomics and Proteomics".

Database UnitProt [Online] Jul. 5, 2004, "SubName: Full=Putative uncharacterized protein".

European Search Report issued Dec. 30, 2009 in PCT/KR2007/006935.

Eggeling (1994) Amino Acids 6:261-272, "Biology of L-lysine overproduction by *Corynebacterium glutamicum*".

Ikeda et al. (Aug. 2003) App. Microbiol. and Biotechnol. 62( 2-3, 1): 99-109, "The *Corynebacterium glutamicum* genome: Features and impacts on biotechnological processes".

Mitsuhashi et al. (Nov. 2006) Biosci., Biotechnol., and Biochem. 70(11): 2803-2806, "Disruption of malate:quinone oxidoreductase increases L-lysine production by *Corynebacterium glutamicum*".

Tzvetkov et al. (Jul. 2003) Microbiology 149(7):1659-1673, "Genetic dissection of trehalose biosynthesis in *Corynebacterium glutamicum*: Inactivation of trehalose production leads to impaired growth and altered cell wall lipid composition".

Accession AXBX248360, Nov. 2006.

Beijer et al. (1992) FEMS Microbiology Letters 100:217-220, "Utilisation of glycerol and glycerol 3-phosphate is differently affected by the phosphotransferase system in *Bacillus subtilis*".

Beijer et al. (Feb. 1993) Journal of General Microbiology, 139(2):349-359, "The *glpP* and *glpF* genes of the glycerol regulon in *Bacillus subtilis*".

Biebl (1998) Appl Microbiol Biotechnol. 50:24-29, "Fermentation of glycerol to 1,3-propanediol and 2,3-butanediol by *Klebsiella pneumonia*".

Doleyres et al. (2005) Appl Microbiol Biotechnol. 68:467-474, "Production of 3-hydroxypropionaldehyde using a two-step process with *Lactobacillus reuteri*".

González-Pajuelo et al. (2004) J Ind Microbiol Biotechnol. 31:442-446, "Production of 1,3-propanediol by *Clostridium butyricum* VPI 3266 using a synthetic medium and raw glycerol".

Kawaguchi et al. (May 2006) Applied and Environmental Microbiology 72(5):3418-3428, "Engineering of a Xylose Metabolic Pathway in *Corynebacterium glutamicum*".

Nishise et al. (1985) Agri. Biol. Chem. 49(3):629-636, "Glycerol Dehydrogenase and Glycerol Dissimilation in *Cellulomonas* sp. NT3060t".

Talarico et al. (Dec. 1988) Antimicrobial Agents and Chemotherapy 32(12):1854-1858, "Production and Isolation of Reuterin, a Growth Inhibitor Produced by *Lactobacillus reuteri*".

Voegele (Feb. 1993) Journal of Bacteriology, 175(4):1087-1094, "Glycerol Kinase of *Escherichia coli* Is Activated by Interaction with the Glycerol Facilitator".

Cerdeno-Tarraga et al. (2003) Nucleic Acids Research 31(22):6516-6523 , "The complete genome sequence and analysis of *Corynebacterium diphtheriae* NCTC13129".

Heller et al. (Oct. 1980) Journal of Bacteriology 144(1):274-278, "Substrate Specificity and Transport Properties of the Glycerol Facilitator of *Escherichia coli*".

Himmi et al. (2000) Appl Microbiol Biotechnol 53:435-440, "Propionic acid fermentation of glycerol and glucose by *Propionbacterium acidipropionici* and *Propionibacterium freudenreichii* ssp. *shennanii*".

International Search Report and Written Opinion dated May 16, 2008 from PCT/KR2008/000391.

Ito et al. (2005) Journal of Bioscience and Bioengineering 100(3):260-265, "Hydrogen and Ethanol Production from Glycerol-Containing Wastes Discharged after Biodiesel Manufacturing Process".

Lin et al. (1976) Ann. Rev. Microbiol. 30:535-578, "Glycerol Dissimilation and its Regulation in Bacteria".

Menzel (1997) Enzyme and Microbial Technology 20:82-86, "High Concentration and Productivity of 1,3-propanediol from continuous fermentation of glycerol by *Klebsiella pneumoniae*".

Parche et al. (Jul. 2001) J. Mol. Microbiol. Biotechnol. 3(3):415-422, "*Corynebacterium diphtheriae*: a PTS View to the Genome".

Paulsen et al. (Oct. 2000) Microbiology146:2343-2344, "Functional genomic studies of dihydroxyacetone utilization in *Escherichia coli*".

Wang et al. (2001) Biotechnology Advances 19:201-223, "Glycerol production by microbial fermentation: A review".

Contador C.A. et al., "Ensemble modeling for strain development of l-lysine-producing *Escherichia coli*," Metabolic Engineering, Jul. 1, 2009, pp. 221-233, vol. 11, No. 4-5, Academic Press.

Koffas Mattheos A.G. et al., "Effect of pyruvate carboxylase overexpression on the physiology of *Corynebacterium glutamicum*," Applied and Environmental Microbiology, Nov. 2002, pp. 5422-5428, vol. 68, No. 11.

Extended European Search Report dated Jan. 5, 2010, for European Patent Application No. 07808268.

International Search Report dated Jan. 2, 2008, for PCT International Patent Application No. PCT/KR2007/004478.

GenBank Accession No. BA000036.3, (2009).

Liebl, W. "Transfer of *Brevibacterium divaricatum* DSM 20297T, "*Brevibacterium flavum*" DSM 20411, "*Brevibacterium lactofermenturn*" DSM 20412 and DSM 1412, and *Corynebacteriumlilium* DSM 20137T to *Corynebacteriurn glutamicum* and Their Distinction by rRNA Gene Restriction Patterns" International Journal of Systematic Bacteriology, 1991, vol. 41, pp. 255-260.

Vertes, A.A. "Transposon Mutagenesis of Coryneform Bacteria" Mol.Gen.Genet., 1994,vol. 245, pp. 397-405.

Moon, et al. (2005) FEMS Microbiology Letters, "Analyses of enzyme II gene mutants for sugar transport and heterologous express of fructokinase gene in *Corynebacterium* glutamicum ATCC 13032," vo. 244, p. 259-266.

\* cited by examiner

SEQUENCE LISTING

<160> NUMBER OF SEQ ID NOS: 22

<210> SEQ ID NO 1
<211> LENGTH: 510
<212> TYPE: DNA
<213> ORGANISM: Corynebacterium glutamicum ATCC13032

<400> SEQUENCE: 1

```
gcagacgcac tcgactacac ctccacctgc ccagaatgct cccaacctgg ggtgtttcgt      60
catcacaccc accggatgct cattgattta cccatcgtcg ggtttcccac caaactgttt     120
atccgtctac ctcgctaccg ctgcaccaac cccacatgta agcaaaagta tttccaagca     180
gaactaagct gcgctgacca cggtaaaaag gtcacccacc gggtcacccg ctggatttta     240
caacgccttg ctattgaccg gatgagtgtt cacgcaaccg cgaaagcact tgggctaggg     300
tgggatttaa cctgccaact agccctcgat atgtgccgtg agctggtcta taacgatcct     360
caccatcttg atggagtgta tgtcattggg gtggatgagc ataagtggtc acataatagg     420
gctaagcatg tgatgggtt tgtcaccgtg attgtcgata tgaccgggca tcggtatgac     480
tcacggtgtc ctgcccggtt attagatgtc                                      510
```

<210> SEQ ID NO 2
<211> LENGTH: 479
<212> TYPE: DNA
<213> ORGANISM: Corynebacterium glutamicum ATCC13032

<400> SEQUENCE: 2

```
aactcattcc ttctgctcgt cgcgtgatgg atccattcca tgttgtgcgg cttgctggtg      60
acaagctcac cgcctgccgg caacgcctcc agcgggagaa ataccagcgt cgtggtttaa     120
gccaggatcc gttgtataaa aaccggaaga ccttgttgac cacgcacaag tggttgagtc     180
ctcgtcagca agaaagcttg gagcagttgt gggcgtatga caaagactac ggggcgttaa     240
agcttgcgtg gcttgcgtat caggcgatta ttgattgtta tcagatgggt aataagcgtg     300
aagcgaagaa gaaaatgcgg accattattg atcagcttcg ggtgttgaag gggccgaata     360
aggaactcgc gcagttgggt cgtagtttgt ttaaacgact tggtgatgtg ttggcgtatt     420
tcgatgttgg tgtctccaac ggtccggtcg aagcgatcaa cggacggttg gagcatttg      479
```

<210> SEQ ID NO 3
<211> LENGTH: 36
<212> TYPE: DNA
<213> ORGANISM: Artificial Sequence
<220> FEATURE:
<223> OTHER INFORMATION: primer

<400> SEQUENCE: 3

```
atcctctaga gtcgaccatc gctgacacca tctgcc                                36
```

<210> SEQ ID NO 4
<211> LENGTH: 38
<212> TYPE: DNA
<213> ORGANISM: Artificial Sequence
<220> FEATURE:
<223> OTHER INFORMATION: primer

<400> SEQUENCE: 4

```
gggcccacta gtctcgagtt caccgcggga gccaagcc                              38
```

<210> SEQ ID NO 5

```
<211> LENGTH: 37
<212> TYPE: DNA
<213> ORGANISM: Artificial Sequence
<220> FEATURE:
<223> OTHER INFORMATION: primer

<400> SEQUENCE: 5
ctcgagacta gtgggccctg gattccaagg ctacgcc                              37

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6
atgcctgcag gtcgaccctg aatggataag gcaccg                               36

<210> SEQ ID NO 7
<211> LENGTH: 37
<212> TYPE: DNA
<213> ORGANISM: Artificial Sequence
<220> FEATURE:
<223> OTHER INFORMATION: primer

<400> SEQUENCE: 7
tgtcgggccc actagttccc agggtagttg actaaag                              37

<210> SEQ ID NO 8
<211> LENGTH: 34
<212> TYPE: DNA
<213> ORGANISM: Artificial Sequence
<220> FEATURE:
<223> OTHER INFORMATION: primer

<400> SEQUENCE: 8
gaatgagttc ctcgagtatc aacgcgtcgg taga                                 34

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gctaccgctg caccaacccc                                                 20

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
ttcacgccga attcgacaag gcaatcaccg                                      30

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
```

-continued

```
tgtcgggccc actagttcat tggcgtttcc ggatcc                          36

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
gaatgagttc ctcgagacaa gcgccaagga actacc                          36

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
acaagcgcca aggaactacc                                            20

<210> SEQ ID NO 14
<211> LENGTH: 46
<212> TYPE: DNA
<213> ORGANISM: Artificial Sequence
<220> FEATURE:
<223> OTHER INFORMATION: primer

<400> SEQUENCE: 14
tgtcgggccc actagtcata tgaataatgt tttatgtatg ggagaa               46

<210> SEQ ID NO 15
<211> LENGTH: 46
<212> TYPE: DNA
<213> ORGANISM: Artificial Sequence
<220> FEATURE:
<223> OTHER INFORMATION: primer

<400> SEQUENCE: 15
gaatgagttc ctcgagatac cattctagag ggcttaaagc taccgg               46

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
ataccattct agagggctta aagctaccgg                                 30

<210> SEQ ID NO 17
<211> LENGTH: 1266
<212> TYPE: DNA
<213> ORGANISM: Corynebacterium glutamicum KCCM10770P

<400> SEQUENCE: 17
gtggccctgg tcgtacagaa atatggcggt tcctcgcttg agagtgcgga acgcattaga    60
aacgtcgctg aacggatcgt tgccaccaag aaggctggaa atgatgtcgt ggttgtctgc   120
tccgcaatgg agacaccac ggatgaactt ctagaacttg cagcggcagt gaatcccgtt    180
ccgccagctc gtgaaatgga tatgctcctg actgctggtg agcgtatttc taacgctctc   240
gtcgccatgg ctattgagtc ccttggcgca gaagcccaat ctttcacggg ctctcaggct   300
```

```
ggtgtgctca ccaccgagcg ccacggaaac gcacgcattg ttgatgtcac tccaggtcgt        360
gtgcgtgaag cactcgatga gggcaagatc tgcattgttg ctggtttcca gggtgttaat        420
aaagaaaccc gcgatgtcac cacgttgggt cgtggtggtt ctgacaccac tgcagttgcg        480
ttggcagctg cttttgaacgc tgatgtgtgt gagatttact cggacgttga cggtgtgtat        540
accgctgacc cgcgcatcgt tcctaatgca cagaagctgg aaaagctcag cttcgaagaa        600
atgctggaac ttgctgctgt tggctccaag attttggtgc tgcgcagtgt tgaatacgct        660
cgtgcattca atgtgccact tcgcgtacgc tcgtcttata gtaatgatcc cggcactttg        720
attgccggct ctatggagga tattcctgtg aagaagcag tccttaccgg tgtcgcaacc         780
gacaagtccg aagccaaagt aaccgttctg ggtatttccg ataagccagg cgaggctgcg        840
aaggttttcc gtgcgttggc tgatgcagaa atcaacattg acatggttct gcagaacgtc        900
tcttctgtag aagacggcac caccgacatc accttcacct gccctcgttc cgacggccgc        960
cgcgcgatgg agatcttgaa gaagcttcag gttcagggca actggaccaa tgtgctttac       1020
gacgaccagg tcggcaaagt ctccctcgtg ggtgctggca tgaagtctca cccaggtgtt       1080
accgcagagt tcatggaagc tctgcgcgat gtcaacgtga acatcgaatt gatttccacc       1140
tctgagattc gtatttccgt gctgatccgt gaagatgatc tggatgctgc tgcacgtgca       1200
ttgcatgagc agttccagct gggcggcgaa gacgaagccg tcgtttatgc aggcaccgga       1260
cgctaa                                                                   1266

<210> SEQ ID NO 18
<211> LENGTH: 1035
<212> TYPE: DNA
<213> ORGANISM: Corynebacterium glutamicum KCCM10770P

<400> SEQUENCE: 18
atgaccacca tcgcagttgt tggtgcaacc ggccaggtcg gccaggttat gcgcacccct         60
ttggaagagc gcaatttccc agctgacact gttcgtttct ttgcttcccc acgttccgca       120
ggccgtaaga ttgaattccg tggcacggaa atcgaggtag aagacattac tcaggcaacc       180
gaggagtccc tcaaggacat cgacgttgcg ttgttctccg ctggaggcac cgcttccaag       240
cagtacgctc cactgttcgc tgctgcaggc gcgactgttg tggataactc ttctgcttgg       300
cgcaaggacg acgaggttcc actaatcgtc tctgaggtga accctccga caaggattcc        360 ctggtcaagg gcattattgc gaaccctaac tgcaccacca tggctgcgat gccagtgctg      420
aagccacttc acgatgccgc tggtcttgta aagcttcacg tttcctctta ccaggctgtt       480
tccggttctg gtcttgcagg tgtggaaacc ttggcaaagc aggttgctgc agttggagac       540
cacaacgttg agttcgtcca tgatggacag gctgctgacg caggcgatgt cggacccttat       600 gtttcaccaa tcgcttacaa cgtgctgcca ttcgccggaa acctcgtcga tgacggcacc       660
ttcgaaaccg atgaagagca gaagctgcgc aacgaatccc gcaagattct cggtctccca       720
gacctcaagg tctcaggcac ctgcgtccgc gtgccggttt tcaccggcca cacgctgacc       780
attcacgccg aattcgacaa ggcaatcacc gtggaccagg cgcaggagat cttgggtgcc       840
gcttcaggcg tcaagcttgt cgacgtccca accccacttg cagctgccgg cattgacgaa       900
tccctcgttg gacgcatccg tcaggactcc actgtcgacg ataaccgcgg tctggttctc      960
gtcgtatctg gcgacaacct ccgcaagggt gctgcgctaa acaccatcca gatcgctgag      1020
ctgctggtta agtaa                                                       1035

<210> SEQ ID NO 19
```

<211> LENGTH: 906
<212> TYPE: DNA
<213> ORGANISM: Corynebacterium glutamicum KCCM10770P

<400> SEQUENCE: 19

```
atgagcacag gtttaacagc taagaccgga gtagagcact tcggcaccgt tggagtagca      60
atggttactc cattcacgga atccggagac atcgatatcg ctgctggccg cgaagtcgcg     120
gcttatttgg ttgataaggg cttggattct ttggttctcg cgggcaccac tggtgaatcc     180
ccaacgacaa ccgccgctga aaaactagaa ctgctcaagg ccgttcgtga ggaagttggg     240
gatcggcgca agctcatcgc cggtgtcgga accaacaaca cgcggacatc tgtggaactt     300
gcggaagctg ctgcttctgc tggcgcagac ggccttttag ttgtaactcc ttattactcc     360
aagccgagcc aagagggatt gctggcgcac ttcggtgcaa ttgctgcagc aacagaggtt     420
ccaatttgtc tctatgacat tcctggtcgg tcaggtattc caattgagtc tgataccatg     480
agacgcctga gtgaattacc tacgattttg gcggtcaagg acgccaaggg tgacctcgtt     540
gcagccacgt cattgatcaa agaaacggga cttgcctggt attcaggcga tgacccacta     600
aaccttgttt ggcttgcttt gggcggatca ggtttcattt ccgtaattgg acatgcagcc     660
cccacagcat tacgtgagtt gtacacaagc ttcgaggaag gcgacctcgt ccgtgcgcgg     720
gaaatcaacg ccaaactatc accgctggta gctgcccaag tcgcttgggt ggagtcagc     780
ttggcaaaag ctgctctgcg tctgcagggc atcaactag gagatcctcg acttccaatt     840
atggctccaa atgagcagga acttgaggct ctccgagaag acatgaaaaa agctggagtt     900
ctataa                                                                906
```

<210> SEQ ID NO 20
<211> LENGTH: 780
<212> TYPE: DNA
<213> ORGANISM: Corynebacterium glutamicum KCCM10770P

<400> SEQUENCE: 20

```
atgggaatca aggttggcgt tctcggagcc aaaggccgtg ttggtcaaac tattgtggca      60
gcagtcaatg agtccgacga tctggagctt gttgcagaga tcgcgtcga cgatgatttg     120
agccttctgg tagacaacgg cgctgaagtt gtcgttgact tcaccactcc taacgctgtg     180
atgggcaacc tggagttctg catcaacaac ggcatttctg cggttgttgg aaccacgggc     240
ttcgatgatg ctcgtttgga gcaggttcgc gactggcttg aaggaaaaga caatgtcggt     300
gttctgatcg cacctaactt tgctatctct gcggtgttga ccatggtctt ttccaagcag     360
gctgcccgct tcttcgaatc agctgaagtt attgagctgc accaccccaa caagctggat     420
gcaccttcag gcaccgcgat ccacactgct cagggcattg ctgcggcacg caaagaagca     480
ggcatggacg cacagccaga tgcgaccgag caggcacttg agggttcccg tggcgcaagc     540
gtagatggaa tcccggttca tgcagtccgc atgtccggca tggttgctca cgagcaagtt     600
atctttggca cccagggtca gaccttgacc atcaagcagg actcctatga tcgcaactca     660
tttgcaccag gtgtcttggt gggtgtgcgc aacattgcac agcacccagg cctagtcgta     720
ggacttgagc attacctagg cctgtaaagg ctcatttcag cagcgggtgg aattttttaa     780
                                                                       780
```

<210> SEQ ID NO 21
<211> LENGTH: 949
<212> TYPE: DNA
<213> ORGANISM: Corynebacterium glutamicum KCCM10770P

<400> SEQUENCE: 21

```
atgaataatg tttatgtat aggagaactt ttaatcgatt ttatatgttc tgatatagat        60
acaactcttt ctaaaggaga aaactttaag aagaaggcag gaggggcacc tgcaaatgta       120
acggcagcaa tttcaaagct tggaggaagt gcgtcttttt taggtaaggt tgggaatgat      180
cccttgggac attttttgaa agagacttta gatgaagtta aggtagatac atcaatgctt      240
attatggata caactcaag tactactctt catttgtgtc acttcaggca aatggtgaaa        300
gagattttgt ctttaatagg ggagcagatg gtcttttaag atatgatgaa ataaatttag      360
ataaagtta ctcaaataaa ataattcact ttggttccgc aactgcttta ttaggtggag        420
aaatgacaga cacttactta agataatgg aggaagcgaa gaaaggggga ataattatat       480
cctttgatcc aaactacaga gataatcttt gggaaaacag aacagaagag tttatagcta      540
tttcacgtag tgcattgaac ttgctgattt tgtgaaatta agtgacgagg aattaaaaat     600
tatatctgga gagaaaaata taaaaatgg agtaaagctt ttagcttcaa ataacaaggt      660
tattgctgta actttaggaa agagggtac tatgatttca aatggagaag aagttgaaat    720
catagagagt ataaaaataa aatctataga ttctaccgga gcaggagatg catttgtggg    780
agcatttctt tataaattgt cagaggcatt agaggcaaga gatattttaa gtgactttaa     840
taaaatcaag gaaaatgttc gctttgcaaa taaggttggt gcaattgtgt gtacaaagct    900
tggtgctata agttctcttc ctagtttaag tgaagttgaa ggtgattag               949
```

```
<210> SEQ ID NO 22
<211> LENGTH: 1311
<212> TYPE: DNA
<213> ORGANISM: Corynebacterium glutamicum ATCC13032
```

<400> SEQUENCE: 22

```
atgaagtcta ccggcaacat catcgctgac accatctgcc gcactgcgga actaggactc      60
accatcaccg gcgcttccga tgcaggtgat tacaccctga tcgaagcaga cgcactcgac     120
tacacctcca cctgcccaga atgctcccaa cctggggtgt tcgtcatca cacccaccgg     180
atgctcattg atttacccat cgtcgggttt cccaccaaac tgtttatccg tctacctcgc    240
taccgctgca ccaaccccac atgtaagcaa agtatttcc aagcagaact aagctgcgct     300
gaccacggta aaaaggtcac ccaccgggtc acccgctgga ttttacaacg ccttgctatt   360
gaccggatga gtgttcacgc aaccgcgaaa gcacttgggc tagggtggga tttaacctgc   420
caactagccc tcgatatgtg ccgtgagctg gtctataacg atcctcacca tcttgatgga  480
gtgtatgtca ttggggtgga tgagcataag tggtcacata atagggctaa gcatggtgat  540
gggtttgtca ccgtgattgt cgatatgacc gggcatcggt atgactcacg gtgtcctgcc  600
cggttattag atgtcgtccc aggtcgtagt gctgatgctt acggtcctg gcttggctcc   660
cgcggtgaac agttccgcaa tcagatacgg atcgtgtcca tggatggatt ccaaggctac  720
gccacagcaa gtaaagaact cattccttct gctcgtcgcg tgatggatcc attccatgtt  780
gtgcggcttg ctggtgacaa gctcaccgcc tgccggcaac gcctccagcg ggagaaatac  840
cagcgtcgtg gtttaagcca ggatccgttg tataaaaacc ggaagacctt gttgaccacg  900
cacaagtggt tgagtcctcg tcagcaagaa gccttggagc agttgtgggc gtatgacaaa  960
gactacgggg cgttaaagct tgcgtggctt gcgtatcagg cgattattga ttgttatcag 1020
atgggtaata gcgtgaagc gaagaagaaa atgcggacca ttattgatca gcttcggtg   1080
ttgaagggggc cgaataagga actcgcgcag ttgggtcgta gtttgtttaa acgacttggt 1140
```

```
gatgtgttgg cgtatttcga tgttggtgtc tccaacggtc cggtcgaagc gatcaacgga    1200
cggttggagc atttgcgtgg gattgctcta ggtttccgta atttgaacca ctacattctg    1260
cggtgcctta tccattcagg gcagttggtc cataagatca atgcactcta a             1311
```

VECTOR FOR TRANSFORMATION USING TRANSPOSONS, MICROORGANISMS TRANSFORMED BY THE VECTOR, AND METHOD FOR PRODUCING L-LYSINE USING THE SAME

THE CROSS-REFERENCE TO RELATED APPLICATIONS (INCORPORATION BY REFERENCE)

The present application is a national phase entry under 35 U.S.C. 371 of International Application No. PCT/KR2009/001845 filed on Apr. 10, 2009, which claims the benefit of Korean Patent Application No. 10-2008-0033054 filed on Apr. 10, 2008. The disclosures of said applications are incorporated by reference herein.

TECHNICAL FIELD

The present invention relates to a vector for transformation using a transposon gene, a microorganism transformed with the said vector, and a preparation method of lysine using the said microorganism.

Incorporated by reference herein in its entirety is the Sequence Listing entitled "Sequence.txt", created Aug. 13, 2010, size of 14 kilobytes.

BACKGROUND ART

*Corynebacterium*, especially *Corynebacterium glutamicum*, is a Gram-positive microorganism used for the production of L-amino acid. L-amino acid, particularly L-lysine, has been widely used for the production of animal feeds, medicines for human, and cosmetics. This amino acid is generated by the fermentation using *Corynebacterium*.

The conventional production method of L-lysine has used *Corynebacterium* having enhanced L-lysine biosynthesis related gene. For example, U.S. Pat. No. 6,746,855 describes a production method of L-lysine by culturing *Corynebacterium* sp. which enhanced the lysine releasing carrier gene lysE and introduced with an additional gene selected from the group consisting of dapA encoding dihydrodipicolinate synthase, lysC encoding aspartate kinase, pyc encoding pyruvate carboxylase and dapB encoding dihydropicolinate reductase. And, U.S. Pat. No. 6,221,636 describes *Corynebacteria* transformed with recombinant DNA containing the DNA sequence encoding diaminopimelate dicarboxylase and the DNA sequence encoding aspartokinase which is substantially insensitive to feedback inhibition by L-lysine and L-threonine.

To enhance the said L-lysine biosynthesis related gene without an antibiotic-resistant sequence, either the number of gene copies is increased or the enzyme activity is increased by mutation. There are two methods reported so far to increase the number of gene copies.

One of the two methods to increase the number of copies is tandem repeat which inserts an additional gene into the right next to the intrinsic gene. The other method is to insert an additional gene into one or more chromosome regions of *Corynebacterium* sp. (U.S. Pat. No. 7,160,711). However, these methods are limited in gene insertion sites, indicating that it is very difficult to insert multiple genes. To overcome this problem, it has been attempted to insert target genes in the region of multiple copies of rDNA on the genome. It was reported that this method was more successful than the previous ones. Nevertheless, this method has still a limitation because the destruction of two or more rDNA copies can affect the growth of the microorganism.

Transposon is also called Insertional Sequence Element, which is the sequence that can be moved on chromosome or on plasmid. Transposon includes transposase, which shows the activity to recognize a specific sequence for the insertion. Up to date, hundreds of transposons have been reported in a variety of bacteria (TRANSPOSON-BASED STRATEGIES FOR MICROBIAL FUNCTIONAL GENOMICS AND PROTEOMICS (2003) Annual Review of Genetics 37: 3-29 Finbarr Hayes).

DISCLOSURE

Technical Problem

The present inventors have tried to develop a strain that can produce lysine at high concentration by using a vector for transformation available for insertion of two or more copies of a target gene regardless of location, without inhibiting the growth of the microorganism. At last, the present inventors completed this invention by confirming that the vector for transformation using a transposon gene was very useful for the insertion of a foreign gene.

Therefore, it is an object of the present invention to provide a vector for transformation using a transposon gene.

It is another object of the present invention to provide a *Corynebacterium* sp. microorganism having improved lysine productivity by being transformed with the said vector for transformation.

It is further an object of the present invention to provide a production method of lysine from the culture solution of the *Corynebacterium* sp. microorganism.

Technical Solution

To achieve the above objects, the present invention provides a vector for transformation containing a transposon gene and a multicloning site.

The present invention also provides a *Corynebacterium* sp. microorganism having improved lysine productivity by being transformed with the said vector for transformation.

The present invention further provides a production method of lysine from the culture solution of the *Corynebacterium* sp. microorganism.

Advantageous Effect

The present invention provides a *Corynebacterium* sp. microorganism capable of producing lysine at high concentration that has improved endogenous activity by inserting aspartate kinase gene (lysC), aspartate semialdehyde dihydrogenase gene (asd), dihydrodipicolinate synthase gene (dapA) and dihydropicolinate reductase gene (dapB) serially in the region of a transposon gene existing as multiple copies on the genome of the *Corynebacterium* sp. microorganism and at the same time has been endowed a novel activity by the additional insertion of fructokinase gene (srk) not existing in *Corynebacteria* in the region of the transposon gene.

DESCRIPTION OF DRAWINGS

The above and other objects, features and advantages of the present invention will become apparent from the following description of preferred embodiments given in conjunction with the accompanying drawings, in which.

BEST MODE

The present invention provides a vector for transformation containing a transposon gene and a multicloning site.

The transposon gene can be originated from *Corynebacterium* sp. *Corynebacterium* sp. microorganism has many different types of transposons. For example, *Corynebacterium glutamicum* ATCC13032 includes 24 transposons, which are classified into 9 groups (The complete *Corynebacterium glutamicum* ATCC 13032 genome sequence and its impact on the production of-aspartate-derived amino acids and vitamins (2003) *Journal of Biotechnology* 104, 5-25 Jorn Kalinowski et al). Among them, ISCg1 and ISGg2 include 4 and 5 copies respectively and each copy shows at least 99% homology.

The transposon gene of the present invention is preferably a member of the group of ISCg1 (SEQ ID. NO: 22) among transposons originated from *Corynebacterium glutamicum* ATCC13032 (GenBank accession NO: NC_003450, NCg11021), and particularly the one that has the nucleotide sequences represented by SEQ ID. NO: 1 and 2.

The said multicloning site is the nucleotide sequence artificially inserted to facilitate the recognition by many restriction enzymes, suggesting that it makes the target gene insertion easy.

The genes that can be inserted in the said multicloning site are aspB (gene encoding aspartate aminotransferase), lysC (gene encoding aspartate kinase), asd (gene encoding aspartate semialdehyde dehydrogenase), dapA (gene encoding dihydrodipicolinate synthase), dapB (gene encoding dihydropicolinate reductase) and lysA (gene encoding diaminodipymalate dicarboxylase), which are endogenous genes of *Corynebacterium* sp. microorganisms involved in the production of L-amino acid. In addition, the exogenous srk (gene encoding fructokinase) can also be inserted.

It is preferable to insert one or more genes selected from the group consisting of aspB, lysC, asd, dapA, dapB and lysA into the said multicloning site. It is also possible to insert the endogenous genes selected above and an exogenous gene together into the multicloning site. It is more preferred to serially insert lysC/asd and dapA/dapB into the multicloning site or possibly the exogenous srk gene that cannot be found in *Corynebacterium* sp. microorganisms is inserted.

In a preferred embodiment of the present invention, the said lysC, asd, dapA, and dapB genes have the nucleotide sequences respectively represented by SEQ ID. NOs: 17, 18, 19, and 20 originated from *Corynebacterium glutamicum* KCCM 10770Pb (GenBank accession number: NC_003450, NCg10247~0248 and NCg11896~1898). The foreign gene srk can be the one that has the nucleotide sequence represented by SEQ ID. NO: 21 originated from *Clostridium acetylbutyricum* ATCC 824 (GenBank accession number: NP_347064).

The genes inserted in the vector for transformation of the present invention can be integrated in the chromosome of *Corynebacterium* sp. microorganism by the secondary crossover.

The vector for transformation using the transposon gene of the present invention is not only able to amplify at least two copies of the endogenous gene but also suitable for the insertion of gene by crossover with high efficiency owing to the multiple transposons. This vector can also be effective in producing a strain that can amplify different genes in a series with the same vector. The transposon is the gene that does not affect the growth of a microorganism and is rather helpful to reduce gene instability. Moreover, it facilitates foreign gene insertion even without a specific target site and it can also be prepared in a series.

The present invention also provides a *Corynebacterium* sp. microorganism having improved lysine productivity by being transformed with the said vector for transformation.

In this invention, the microorganism having lysine productivity that can be transformed by the vector for transformation of the present invention can be any of those *Corynebacterium* sp. microorganisms. For example, the *Corynebacterium* sp. microorganism that is available for this invention is *Corynebacterium glutamicum* ATCC 13032 or *Corynebacterium thermoaminogenes* FERM BP-1539. Besides, the L-amino acid producing mutants or strains generated therefrom, for example *Corynebacterium glutamicum* KFCC10881, *Corynebacterium glutamicum* KFCC 11001 and *Corynebacterium glutamicum* KCCM 10770 are also available. Most preferably, the microorganism is *Corynebacterium glutamicum* KCCM 10770P.

Figure 2:
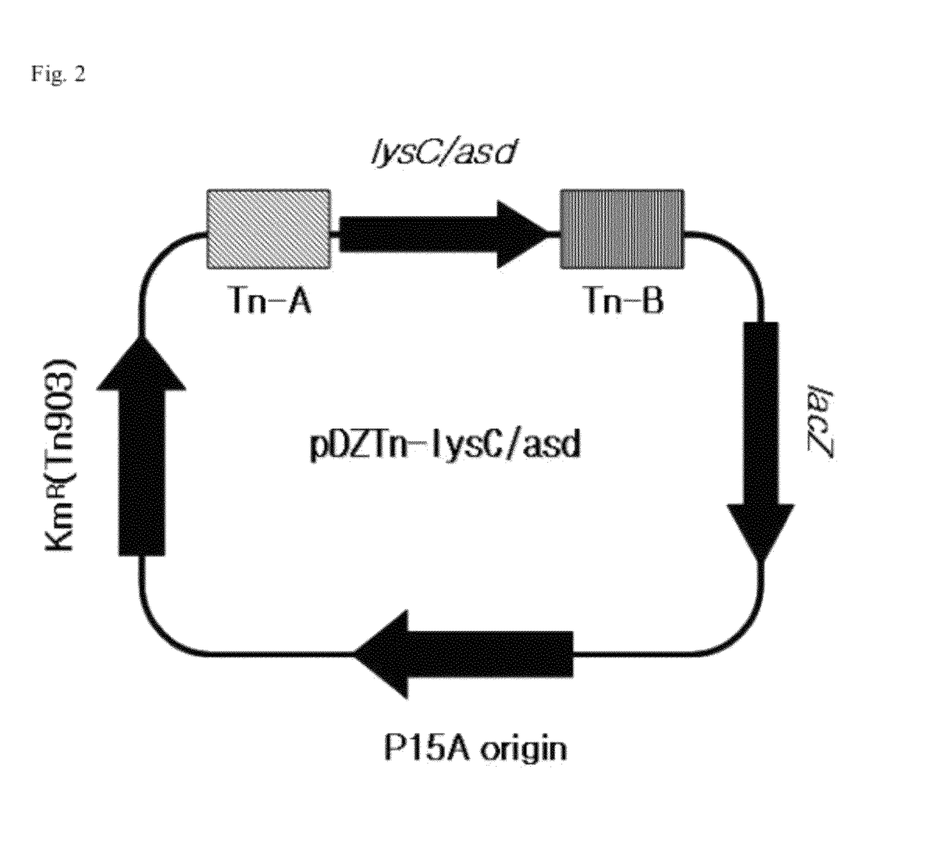
FIG. 2 is a diagram illustrating the *Corynebacterium* chromosome insertion vector pDZTn-lysC/asd.
Figure 3:
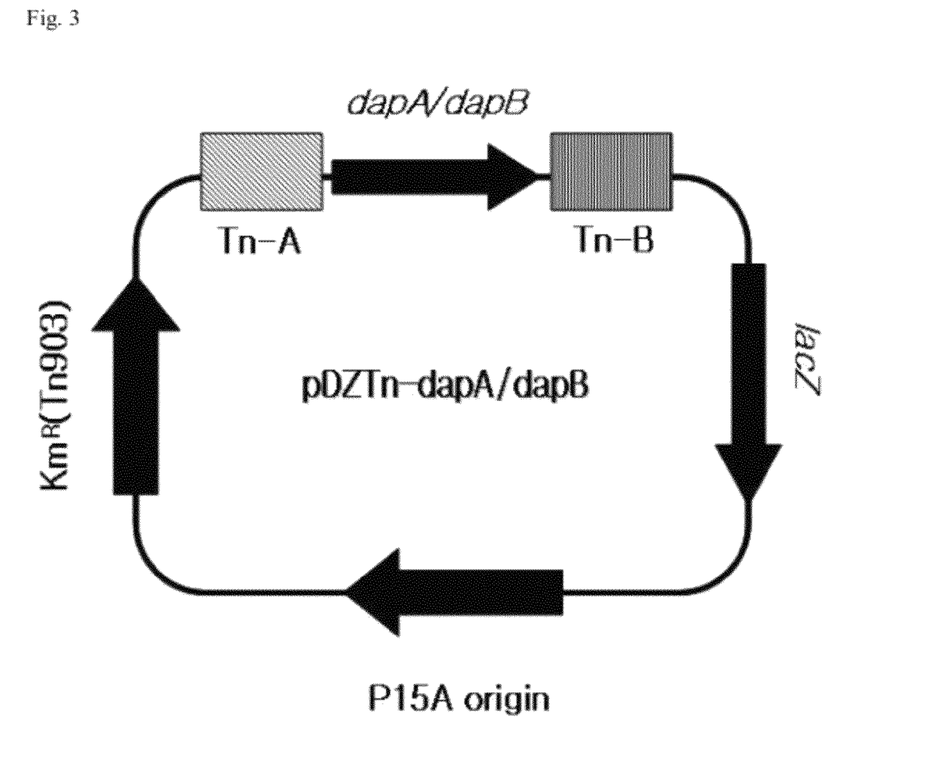
FIG. 3 is a diagram illustrating the *Corynebacterium* chromosome insertion vector pDZTn-dapA/dapB.
Figure 4:
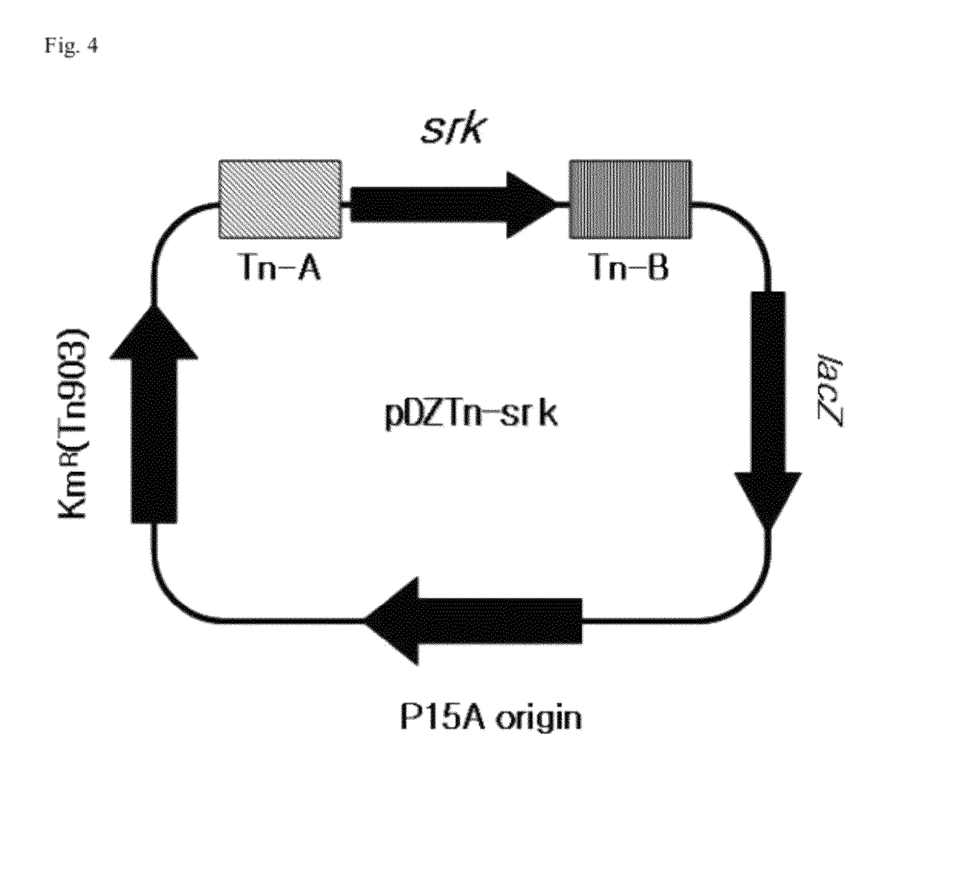
FIG. 4 is a diagram illustrating pDZTn-srk vector.

In a preferred embodiment of the present invention, the *Corynebacterium* sp. microorganism of the invention can be transformed by the vector for transformation pDZTn-lscC/asd, pDZTndapA/dapB or pDZTn-crk having the cleavage map of FIG. 2, 3, or 4. The said vector for transformation can be inserted in the *Corynebacterium* sp. microorganism orderly or simultaneously. The insertion of the vector into chromosome can be performed by the method well-known to those in the art such as homologous recombination.

The present invention further provides a production method of lysine from the culture solution of the *Corynebacterium* sp. microorganism.

The culture of L-lysine using the *Corynebacterium* sp. microorganism can be performed by the conventional method well-known to those in the art. For example, the culture herein can be performed by fed batch or repeated fed batch process.

The medium used for the culture herein has to fit the condition required for the specific strain by a required process. The culture medium for the *Corynebacterium* sp. strain is well informed (for example, Manual of Methods for General Bacteriology. American Society for Bacteriology. Washington D.C., USA, 1981).

The usable glycogen is exemplified by carbohydrate such as glucose, sucrose, lactose, fructose, maltose, starch, cellulose; oil and fat such as soybean oil, sunflower oil, castor oil and coconut oil; fatty acid such as palmitic acid, stearic acid, and linoleic acid; alcohol such as glycerol and ethanol; and organic acid such as acetic aid. One of these compounds or a mixture thereof can be used.

The usable nitrogen source is exemplified by such organic nitrogen source as peptone, yeast extract, gravy, malt extract, corn steep liquor and bean flour and such inorganic nitrogen source as urea, ammonium sulfate, ammonium chloride, ammonium phosphate, ammonium carbonate and ammonium nitrate. One of these compounds or a mixture thereof can be used as a nitrogen source.

The medium herein can additionally include potassium dihydrogen phosphate, dipotassium hydrogen phosphate and corresponding sodium-containing salts as a phosphate source. The medium can also include a metal salt such as magnesium sulfate or iron sulfate. In addition, amino acids, vitamins and proper precursors can be added as well. The medium or the precursor can be added to the culture by batch-type or continuously. pH of the culture can be adjusted during the cultivation by adding such a compound as ammonium hydroxide, potassium hydroxide, ammonia, phosphoric acid and sulfuric acid. The generation of air bubbles can be inhibited during the cultivation by using an antifoaming agent such as fatty acid polyglycol ester. To maintain aerobic condition of the culture, oxygen or oxygen-containing gas (eg, air) can be injected into the culture. The temperature of the culture is preferably 20-45° C., more preferably 25-40° C. The cultivation can be continued until the production of L-amino acid reaches a wanted level, and the preferable culture time is 10-160 hours. L-lysine is released in the culture medium or can be included in cells.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES

Example 1

Construction of the Vector (pDZTn) Introduced with Transposon Gene and the Method for the Gene Insertion using the Vector In this example, pDZ vector for the insertion of chromosome of *Corynebacterium* sp. microorganism was used as a basic vector to construct the vector pDZTn introduced with the transposon gene of *Corynebacterium* sp. The construction process is as follows.

To obtain transposon gene, the nucleotide sequence information about the transposon gene (NCBI accession NO. NC_003450, NCgI1021) of the total nucleotide sequence originated from *Corynebacterium glutamicum* ATCC13032 was obtained from NIH GenBank, from which two pairs of primers (Table 1, SEQ ID. NO: 3-6) were synthesized.

PCR was performed using the chromosome DNA of *Corynebacterium glutamicum* ATCC13032 as a template and using the oligonucleotides represented by SEQ ID. NO: 3-6 as primers. PfuUltra™ high-confident DNA polymerase (Stratagene) was used as a polymerase. PCR conditions were as follows; denaturation at 96° C. for 30 seconds, annealing at 58° C. for 30 seconds, polymerization at 72° C. for 1 minute, and 30 cycles from denaturation to polymerization.

TABLE 1

| Primer | Sequence | SEQ ID. NO: |
|---|---|---|
| Tn-A-F | atcctctagagtcgaccatcgctgacaccatctgcc | 3 |
| Tn-A-R | gggcccactagtctcgagttcaccgcgg-gagccaagcc | 4 |
| Tn-B-F | ctcgagactagtgggccctggattccaaggctacgc | 5 |
| Tn-B-R | atgcctgcaggtcgaccctgaatggataaggcaccg | 6 |

As a result, two pairs of transposon genes (Tn-A, Tn-B) containing approximately 500 bp long promoter region were obtained. Tn-A (SEQ ID. NO: 1) was amplified by using the sequences represented by SEQ ID. NO: 3 and 4 as primers, while Tn-B (SEQ ID. NO: 2) was amplified by using the sequences represented by SEQ ID. NO: 5 and 6 as primers. The amplified products were cloned into pDZ vector pretreated with Sal I restriction enzyme using BD in-Fusion kit (BD), resulting in the construction of pDZTn vector. There are numbers of restriction enzyme recognition sites which is artificially inserted during the primer construction in between the two amplified products.

Figure 1:
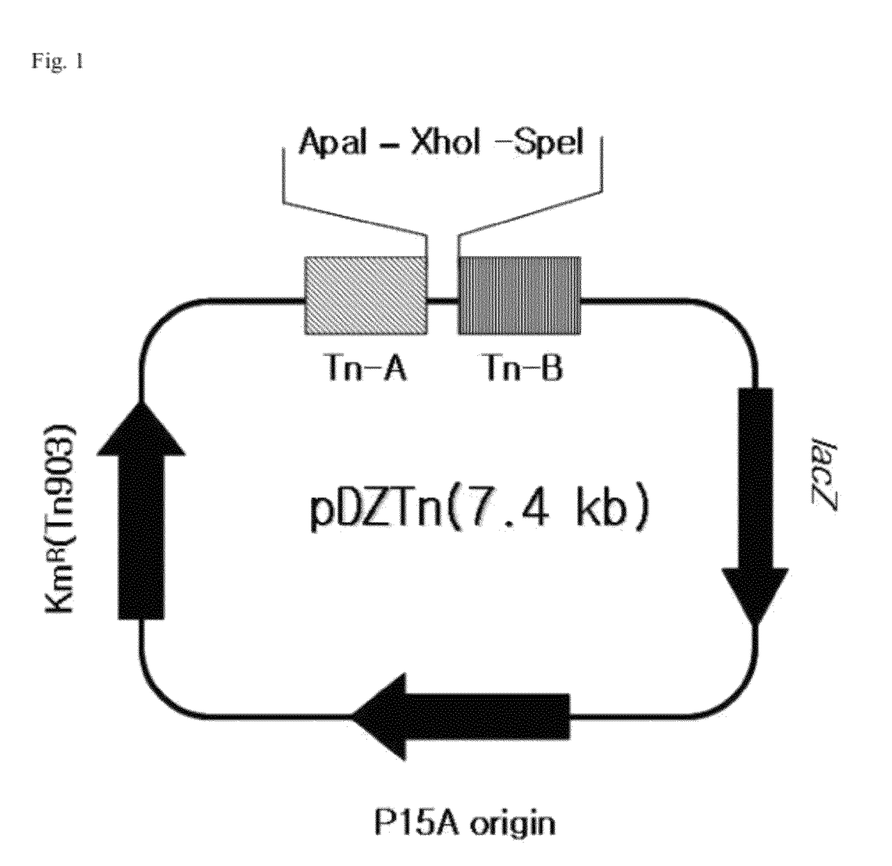
FIG. 1 is a diagram illustrating the *Corynebacterium* chromosome insertion vector pDZTn.

FIG. 1 is a diagram illustrating the *Corynebacterium* chromosome insertion vector pDZTn.

*Corynebacterium glutamicum* KCCM10770P, the patent-granted lysine production strain was transformed with the pDZTn vector constructed by inserting the target gene (Tn-A and Tn-B) (using the transformation method of Appl. Microbiol. Biotechnol. (1999) 52:541-545). Then, the strain having the target gene inserted by gene homology on the chromosome was selected from the selection medium containing 25 mg/L of kanamycin. The successful insertion of the vector in the chromosome was confirmed by observing if the colony was blue on the solid medium containing X-gal (5-bromo-4-chloro-3-indolyl-β-D-galactoside). The primary chromosome inserted strain was shaking-cultured in a nutrient medium (30° C., 8 hours), which was then diluted from $10^{-4}$ to $10^{-10}$, followed by distribution on the solid medium containing X-gal. While most colonies were blue, there were some colonies that were white. Those low rate white colonies were selected, which proceeded to the selection of the strain whose vector sequence inserted on the chromosome was eliminated by the secondary crossover.

Example 2

Cloning of lysC/asd Originated from the Lysine Production Strain *Corynebacterium glutamicum* KCCM10770P, Construction of the Recombinant Vector (pDZTn-lysC/asd), and Development of the lysC/asd Inserted Strain To obtain lysC/asd gene originated from *Corynebacterium glutamicum* KCCM10770P, nucleotide sequence information of lysC/asd (NCBI accession NO. NC_003450, Ncgl0247~0248) was obtained from NIH GenBank, from which a pair of primers (Table 2, SEQ ID. NO: 7 and 8) was synthesized.

PCR was performed using the chromosome DNA of *Corynebacterium glutamicum* KCCM10770P as a template and using the oligonucleotides represented by SEQ ID. NO: 7 and 8 as primers. PfuUltra™ high-confident DNA polymerase (Stratagene) was used as a polymerase. PCR conditions were as follows; denaturation at 96° C. for 30 seconds, annealing at 52° C. for 30 seconds, polymerization at 72° C. for 3 minutes, and 30 cycles from denaturation to polymerization.

TABLE 2

| Primer | Sequence | SEQ ID. NO: |
|---|---|---|
| lysC-F1 (SpeI) | tgtcgggcccactagttcccagggtagttgactaaag | 7 |
| asd-R1 (XhoI) | gaatgagttcctcgagtatcaacgcgtcggtaga | 8 |

As a result, lysC/asd gene containing 2,805 bp long promoter region was separated. The amplified product was cloned into pDZTn vector pretreated with Spe I and Xho I using BD in-Fusion kit, resulting in the construction of the recombination vector pDZTn-lysC/asd. FIG. 2 is a diagram illustrating the *Corynebacterium* chromosome insertion vector pDZTn-lysC/asd.

*Corynebacterium glutamicum* KCCM10770P, the patent-granted lysine production strain was transformed with the constructed vector pDZTn-lysC/asd. After the secondary crossover, a copy of lysC/asd gene was additionally inserted in between transposons on the chromosome. As a result, the lysine production strain *Corynebacterium glutamicum* KCCM10770P-CJ1 having three copies of the gene was prepared. To confirm the strain, PCR was performed using primer 9 and primer 10 (Table 3) facilitating the amplification of the joining region between the transposon and lysC/asd gene.

TABLE 3

| Primer | Sequence | SEQ ID. NO: |
|---|---|---|
| Tn-A-F | gctaccgctgcaccaacccc | 9 |
| asd-1 | ttcacgccgaattcgacaaggcaatcaccg | 10 |

Example 3

Cloning of dapA/dapB Originated from the Lysine Production Strain *Corynebacterium glutamicum* KCCM10770P, Construction of the Recombinant Vector (pDZTn-dapA/dapB), and Development of the dapA/dapB Inserted Strain To obtain dapA/dapB gene originated from *Corynebacterium glutamicum* KCCM 10770P by the same manner as described in example 2, nucleotide sequence information of dapA/dapB (NCBI accession NO. NC_003450, Ncg11896~1898) was obtained from NIH GenBank. As a result, it was confirmed that dapA composed operon along with dapB, between which there was ORF (Ncg11987) whose functions had not been disclosed, yet. Therefore, to amplify the total gene dapB-ORF (Ncg11897)-dapA containing dapB promoter region, two pairs of primers were synthesized (Table 4, SEQ ID. NO: 11-12).

PCR was performed using the chromosome DNA of *Corynebacterium glutamicum* KCCM10770P as a template and using the oligonucleotides represented by SEQ ID. NO: 11-12 as primers. PfuUltra™ high-confident DNA polymerase (Stratagene) was used as a polymerase. PCR conditions were as follows; denaturation at 96° C. for 30 seconds, annealing at 52° C. for 30 seconds, polymerization at 72° C. for 3 minutes, and 30 cycles from denaturation to polymerization.

TABLE 4

| Primer | Sequence | SEQ ID. NO: |
|---|---|---|
| dapA-F (SpeI) | tgtcgggcccactagttcattggcgtttccggatcc | 11 |
| dapA-R (XhoI) | gaatgagttcctcgagacaagcgccaaggaactacc | 12 |

As a result, dapA/dapB gene containing 3,210 bp long promoter region was separated. The amplified product was cloned into pDZTn vector pretreated with Spe I and Xho I using BD in-Fusion kit, resulting in the construction of the recombination vector pDZTn-dapA/dapB. FIG. 3 is a diagram illustrating the *Corynebacterium* chromosome insertion vector pDZTn-dapA/dapB.

The lysine production strain *Corynebacterium glutamicum* KCCM10770P-CJ1 prepared in example 2 was transformed with the constructed vector pDZTn-dapA/dapB. After the secondary crossover, a copy of dapA/dapB gene was additionally inserted in between transposons on the chromosome. As a result, the lysine production strain *Corynebacterium glutamicum* KCCM10770P-CJ2 having three copies of the gene was prepared. To confirm the strain, PCR was performed using primer 9 and primer 13 (Table 5) facilitating the amplification of the joining region between the transposon and dapA/dapB gene.

The said *Corynebacterium glutamicum* KCCM10770P-CJ2 was deposited at Korean Culture Center of Microorganisms, the international depository authority, located at 361-221, Hongje-1-dong, Seodaemun-gu, Seoul, Korea on Mar. 31, 2008 under the Accession number KCCM 10939P.

TABLE 5

| Primer | Sequence | SEQ ID. NO: |
|---|---|---|
| Tn-A-F | gctaccgctgcaccaacccc | 9 |
| dapA-1 | acaagcgccaaggaactacc | 13 |

Example 4

Cloning of srk Originated from *Clostridium acetobutylicum*, Construction of the Recombinant Vector (pDZTn-srk) and Development of the srk Inserted Strain The nucleotide sequence of fructokinase gene originated from *Clostridium acetobutylicum* ATCC 824 has been well-known. The present inventors obtained the gene information of fructokinase originated from *Clostridium acetobutylicum* ATCC 824 from NIH GenBank (Accession NO. NP 347064). A pair of primers (Table 6, SEQ ID. NO: 14 and 15) was synthesized according to the obtained nucleotide sequence. PCR was performed using the chromosome DNA of *Clostridium acetobutylicum* ATCC 824 as a template to amplify the gene. PCR conditions were as follows; denaturation at 94° C. for 20 seconds, annealing at 52° C. for 20 seconds, polymerization at 72° C. for 1 minute and 10 seconds, and 30 cycles from denaturation to polymerization.

TABLE 6

| Primer | Sequence | SEQ ID. NO: |
|---|---|---|
| Srk-F (SpeI) | tgtcgggcccactagtcatatgaataatgttttatgtatgggagaa | 14 |
| srk-R (XhoI) | gaatgagttcctcgagataccattctagagggcttaaagctaccgg | 15 |

As a result, srk gene containing 1,200 bp long promoter region was separated. The amplified product was cloned into pDZTn vector pretreated with Spe I and Xho I using BD in-Fusion kit, resulting in the construction of the recombination vector pDZTn-srk. FIG. 4 is a diagram illustrating the *Corynebacterium* chromosome insertion vector pDZTn-srk.

The patent-granted lysine production strain *Corynebacterium glutamicum* KCCM10770P was transformed with the constructed vector pDZTn-srk. After the secondary crossover, a copy of srk gene was inserted in between transposons on the chromosome. As a result, the lysine production strain *Corynebacterium glutamicum* KCCM10770P-CJ3 was prepared. To confirm the strain, PCR was performed using primer 9 and primer 16 (Table 7) facilitating the amplification of the joining region between the transposon and srk gene.

TABLE 7

| Primer | Sequence | SEQ ID. NO: |
|---|---|---|
| Tn-A-F | gctaccgctgcaccaacccc | 9 |
| Srk-1 | ataccattctagagggcttaaagctaccgg | 16 |

Example 5

Measurement of Aspartate Kinase Activity of the L-Lysine Biosynthesis Gene Multiple-Inserted Strain Aspartate kinase activity of the L-lysine production strain *Corynebacterium glutamicum* KCCM10770P-CJ2 was measured by using aspartyl hydroxamate (Pecher J-F, Capony J-P (1968) On the colorimetric determination of acyl phosphates. Anal Biochem 22: 536~539). As a result, *Corynebacterium glutamicum* KCCM10770P-CJ2 demonstrated 2.1 times higher aspartate kinase activity than the mother strain *Corynebacterium glutamicum* KCCM10770P.

TABLE 8

|  | Activity | Times |
|---|---|---|
| KCCM10770P | 26.77 | 1.00 |
| KCCM10770P-CJ2 | 56.25 | 2.10 |

Example 6

Measurement of Fructokinase Activity of the srk Gene Inserted Strain

It was investigated whether or not fructokinase was expressed in the cells from the fructokinase expression vector and whether or not there was fructokinase activity, by the known method (Andreas Pikis et al, *Microbiology*, 148, 843-852 (2002)). *Corynebacterium glutamicum* KCCM10770P-CJ3 was cultured in LB for one day, followed by centrifugation to obtain the cells. The obtained cells were suspended in a proper buffer, followed by sonication to lysis the cells. Ultra-centrifugation was performed to obtain supernatant. The obtained supernatant was reacted with the reaction solution containing fructose, phosphoglucose, isomerase, glucose-6-phosphate dehydrogenase, ATP and NADP$^+$. The generated NADPH was quantified by measuring $OD_{340}$ with a spectrophotomer, from which fructokinase activity was indirectly calculated. The results are shown in Table 9. As shown in Table 11, *Corynebacterium glutamicum* KCCM10770P-CJ3 demonstrated the fructokinase activity at least double the activity of the mother strain *Corynebacterium glutamicum* KCCM10770P, suggesting that the fructokinase gene was expressed therein.

TABLE 9

| Test Strain | KCCM10770P | KCCM10770P-CJ3 |
|---|---|---|
| Activity$^a$ | 5.14 | 12.13 |

$^a$nmol (generated fructose-6-phosphate) min$^{-1}$mg (protein)$^{-1}$

Example 7

Production of L-Lysine in the L-Lysine Biosynthesis Gene Multiple-Inserted Strain The L-lysine production strain *Corynebacterium glutamicum* KCCM10770P-CJ2 prepared in example 3 was cultured as follows for the production of L-lysine.

*Corynebacterium glutamicum* KCCM10770P-CJ2 and the mother strain *Corynebacterium glutamicum* KCCM10770P were inoculated in a 250 ml corner-baffled flask containing 25 ml of seed culture medium, followed by shaking-culture at 30° C. for 20 hours with 200 rpm. 1 ml of the seed culture medium was inoculated in a 250 ml corner-baffled flask containing 24 ml of production medium, followed by shaking-culture at 30° C. for 120 hours with 200 rpm.

Upon completion of the culture, L-lysine production was measured by the method using HPLC. The amounts of L-lysine in culture solutions of *Corynebacterium glutamicum* KCCM10770P and *Corynebacterium glutamicum* KCCM10770P-CJ2 are shown in Table 10.

TABLE 10

|  | Lysine (g/L) | | |
|---|---|---|---|
| Strain | Batch 1 | Batch 2 | Batch 3 |
| KCCM10770P | 46.1 | 45.8 | 45.4 |
| KCCM10770P-CJ2 | 51.8 | 51.2 | 51.7 |

Seed Culture Medium (pH 7.0)

raw sugar 20 g, pepton 10 g, yeast extract 5 g, urea 1.5 g, $KH_2PO_4$ 4 g, $K_2HPO_4$ 8 g, $MgSO_4 \cdot 7H_2O$ 0.5 g, biotin 100 μg, thiamine HCl 1000 μg, calcium-pantothenate 2000 μg, nicotinamide 2000 μg (in distilled water 1 L)

Production Medium (pH 7.0)

glucose 100 g, $(NH_4)_2SO_4$ 40 g, soybean protein 2.5 g, corn steep solids 5 g, urea 3 g, $KH_2PO_4$ 1 g, $MgSO_4 \cdot 7H_2O$ 0.5 g, biotin 100 μg, thiamine hydrochloride 1000 μg, calcium-pantothenate 2000 μg, nicotinamide 3000 μg, $CaCO_3$ 30 g (in distilled water 1 L)

As shown in Table 10, lysine production by *Corynebacterium glutamicum* KCCM10770P-CJ2 which is inserted two lysine biosynthesis genes was increased 10% from that of the mother strain KCCM 10770P.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A vector for transformation comprising two nucleotide sequences derived from a transposon gene and a multicloning site between said nucleotide sequences, wherein the first nucleotide sequence comprises the sequence represented by SEQ ID NO: 1 and the second nucleotide sequence comprises the sequence represented by SEQ ID NO: 2.

2. The vector for transformation according to claim 1, wherein one or more genes selected from the group consisting of lysC gene encoding aspartate kinase, asd gene encoding aspartate semialdehyde dihydrogenase, dapA gene encoding dihydrodipicolinate synthase, and dapB gene encoding dihydropicolinate are inserted in the multicloning site.

3. The vector for transformation according to claim 1, wherein foreign srk gene encoding fructokinase obtained from *Clostridium acetobutylicum* ATCC 824 is inserted in the multicloning site.

4. A *Corynebacterium glutamicum* having L-lysine productivity, which is transformed with a vector for transformation comprising two nucleotide sequences derived from a transposon gene and a multicloning site between said nucleotide sequences, wherein the first nucleotide sequence comprises the sequence represented by SEQ ID NO: 1 and the second nucleotide sequence comprises the sequence represented by SEQ ID NO: 2.

5. The *Corynebacterium glutamicum* according to claim 4, wherein the *Corynebacterium glutamicum* is *Corynebacterium glutamicum* KCCM10770P-CJ2 (Accession NO: KCCM10939P).

6. The *Corynebacterium glutamicum* having L-lysine productivity according to claim 4, wherein the gene inserted in the multicloning site of the vector for transformation is integrated in the chromosome by the secondary crossover.

7. A method for producing L-lysine containing the steps of culturing a *Corynebacterium glutamicum* having L-lysine productivity, which is characteristically transformed with a vector for transformation comprising two nucleotide sequences derived from a transposon gene and a multicloning site between said nucleotide sequences, wherein the first nucleotide sequence comprises the sequence represented by SEQ ID NO: 1 and the second nucleotide sequence comprises the sequence represented by SEQ ID NO: 2 to produce L-lysine in cells or a culture; and recovering lysine from the cells or from the culture.

8. The *Corynebacterium glutamicum* having L-lysine productivity of claim 4 wherein one or more genes selected from the group consisting of lysC gene encoding aspartate kinase, asd gene encoding aspartate semialdehyde dihydrogenase, dapA gene encoding dihydrodipicolinate synthase, and dapB gene encoding dihydropicolinate are inserted in the multicloning site.

9. The *Corynebacterium glutamicum* having L-lysine productivity of claim 4 wherein foreign srk gene encoding fructokinase obtained from *Clostridium acetobutylicum* ATCC 824 is inserted in the multicloning site.

10. The method for producing L-lysine of claim 7 wherein the transformed microorganism is *Corynebacterium glutamicum* KCCM10770P.

11. The method for producing L-lysine of claim 7 wherein the *Corynebacterium glutamicum* is Corynebacterium glutamicum KCCM10770P-CJ2 (Accession NO: KCCM10939P).

12. The method for producing L-lysine of claim 7 wherein the gene inserted in the multicloning site of the vector for transformation is integrated in the chromosome by the secondary crossover.

13. The method for producing L-lysine of claim 7 wherein one or more genes selected from the group consisting of lysC gene encoding aspartate kinase, asd gene encoding aspartate semialdehyde dihydrogenase, dapA gene encoding dihydrodipicolinate synthase, and dapB gene encoding dihydropicolinate originated from *Corynebacterium* sp, microorganism are inserted in the multicloning site.

14. The method for producing L-lysine of claim 7 wherein srk gene encoding foreign fructokinase obtained from *Clostridium acetobutylicum* ATCC 824 is additionally inserted in the multicloning site.

* * * * *